United States Patent [19]

Tieman

[11] 4,211,780

[45] Jul. 8, 1980

[54] 2,2-(THIOBIS(NITROMETHYLIDYNE))BIS(-TETRAHYDRO-2H-1,3-THIAZINE) AND USE

[75] Inventor: Charles H. Tieman, Modesto, Calif.

[73] Assignee: Shell Oil Company, Houston, Tex.

[21] Appl. No.: 33,934

[22] Filed: Apr. 27, 1979

[51] Int. Cl.² .................... A01N 9/12; C07D 279/06
[52] U.S. Cl. ....................................... 424/246; 544/55
[58] Field of Search .................... 544/54, 55; 424/246

[56] References Cited

U.S. PATENT DOCUMENTS 3,993,648  11/1976  Powell ........................... 260/243 R

*Primary Examiner*—Henry R. Jiles
*Assistant Examiner*—R. W. Ramsuer

[57] ABSTRACT

2,2'-(Thiobis(nitromethylidyne))bis(tetrahydro-2H-1,3-thiazine), useful as an insecticide.

3 Claims, No Drawings

2,2-(THIOBIS(NITROMETHYLIDYNE))BIS(TETRAHYDRO-2H-1,3-THIAZINE) AND USE

DESCRIPTION OF THE INVENTION

It has been found that 2,2'-(thiobis(nitromethylidyne))bis(tetrahydro-2H-1, 3-thiazine), having the formula

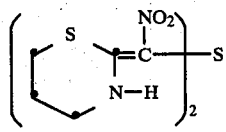

possesses very high toxicity with respect to the corn earworm.

To avoid repetition of its long chemical name, this compound will be referred to hereinafter as "Compound I".

Compound I has been prepared as follows 8.0 g of tetrahydro-2-(nitromethylene)-2H-1,3-thiazine (U.S. Pat. No. 3,993,648), 5.1 g. (7 ml) of triethylamine, and 100 ml of methylene chloride were mixed. The resulting solution was cooled to 5° C. and 2.6 g. (1.6 ml) of sulfur dichloride was added drop by drop over a 15-minute period, at 5°–8° C. The reaction was mildly exothermic. The mixture was stirred for 1.75 hours at about 5° C., and then was poured into cold water. The resulting mixture was filtered. The filter cake was washed with water, and then with methylene chloride to leave a light yellow solid, mp: 142° (with decomposition). Appropriate chemical and spectral analyses confirmed the identity of the product as Compound I.

The activity of Compound I with respect to the corn earworm, *Heliothis zea*, was determined as follows: in each of several replicates, five third-instar corn earworm larvae were placed in a cage upon a cut stem broad bean plant that had been freshly and thoroughly sprayed with a formulation of Compound I. The formulation was prepared by adding two milliliters of a one percent w/v acetone solution of Compound I to eight milliliters of water containing 0.05% of a surfactant, and for ascertaining dosage/mortality relationships, preparing a series of dosages by diluting the resulting solution with appropriate further amounts of the surfactant solution. Preliminary dosage range-finding tests were followed by tests establishing dosage/mortality relationships, the latter being carried out on different days. A standard solution of 0.22% w/v of parathion in the surfactant solution, and appropriate dilutions thereof also were used for comparison. About 48 hours after the larvae were placed upon the plants, the numbers of dead and moribund larvae were noted and the percent mortality was calculated. The toxicity of Compound I was compared against that of the parathion standard and expressed as a toxicity index (J. Econ. Ent., 43–53 (1950)) which was calculated as follows:

$$\text{Toxicity Index (T.I.)} = \frac{LC_{50} \text{ of standard}}{LC_{50} \text{ of test chemical}} \times 100$$

Where "$LC_{50}$" is the concentration of the compound required to kill 50% of the larvae, as determined by plotting the dosage/mortality data on log probit paper.

The toxicity index for Compound I was found to be 1200.

The invention includes within its scope insecticidal compositions comprising an adjuvant—that is, a carrier, optionally a surface-active agent—and, as active ingredient, Compound I. Likewise, the invention includes also a method of combatting insect pests at a locus which comprises applying to the locus an effective amount of Compound I.

The term "carrier" as used herein means a solid or fluid material, which may be inorganic or organic and synthetic or natural origin, with which Compound I is mixed or formulated to facilitate its application to the plant to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates an aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying Compound I to control insects comprises applying it, ordinarily in a composition of one of the aforementioned types, to a locus to be protected from insects, such as the foliage and/or the fruit of plants. It is of course applied in an amount sufficient to exert the desired action. This dosage is dependent upon many factors, including the carrier employed, the method and conditions of the application, whether the formulation is present at the locus in the form of an aerosol, or as a film, or as discrete particles, the thickness of film or size or particles, and the like, proper consideration and resolution of these factors to provide the necessary dosage of active material at the locus to be protected being within the skill of those versed in the art. In general, however, the effective dosage of Compound I at the locus to be protected—i.e., the dosage which the insects contact—is of the order of 0.001 to 0.05% based on the total weight of the formulation, though under some circumstances the effective concentration will be as little as 0.0001% or as much as 2%, on the same basis.

I claim:

1. 2,2′-(Thiobis(nitromethylidyne))bis(tetrahydro-2H-1,3-thiazine).

2. A composition adapted for controlling corn earworms which comprises an effective dosage of the compound of claim 1 together with an adjuvant therefor.

3. A method for protecting plants from attack by corn earworm larvae which comprises applying to the plants to be protected an effective dosage of the compound of claim 1.

* * * * *